US012333726B2

(12) United States Patent
Hirai et al.

(10) Patent No.: US 12,333,726 B2
(45) Date of Patent: Jun. 17, 2025

(54) SPECIMEN ANALYSIS METHOD AND IMAGE PROCESSING METHOD (71) Applicants: SCREEN Holdings Co., Ltd., Kyoto (JP); Kyoto Prefectural Public University Corporation, Kyoto (JP)

(72) Inventors: Maki Hirai, Kyoto (JP); Hiroshi Ogi, Kyoto (JP); Shunta Ishihara, Kyoto (JP); Takahiro Tsujikawa, Kyoto (JP); Kyoko Itoh, Kyoto (JP)

(73) Assignees: SCREEN Holdings Co., Ltd., Kyoto (JP); Kyoto Prefectural Public University Corporation, Kyoto (JP)

( * ) Notice: Subject to any disclaimer, the term of this patent is extended or adjusted under 35 U.S.C. 154(b) by 315 days.

(21) Appl. No.: 17/405,843

(22) Filed: Aug. 18, 2021

(65) Prior Publication Data
US 2022/0067938 A1 Mar. 3, 2022

(30) Foreign Application Priority Data
Aug. 25, 2020 (JP) ................. 2020-141765

(51) Int. Cl.
*G06T 7/00* (2017.01)
*G01N 15/01* (2024.01)
(Continued)

(52) U.S. Cl.
CPC ....... *G06T 7/0014* (2013.01); *G01N 15/1429* (2013.01); *G06T 7/187* (2017.01);
(Continued)

(58) Field of Classification Search
CPC .......... A61B 5/00; G06T 7/00; G06T 7/0014; G06T 7/187; G06T 7/30;
(Continued)

(56) References Cited

U.S. PATENT DOCUMENTS 7,372,985 B2 * 5/2008 So ................ G06V 20/69
382/133
7,756,305 B2 * 7/2010 Price ............ G06T 5/75
382/128
(Continued)

FOREIGN PATENT DOCUMENTS

CN 111260677 A 6/2020
EP 3 232 402 A1 10/2017
(Continued)

OTHER PUBLICATIONS

Tleis et al. "Contour expansion algorithm preprocessed by hough transform and circular shortest path for ovoid objects." 2015 International Conference on Image Processing Theory, Tools and Applications (IPTA). IEEE, 2015. • Conclusion: (Year: 2015).*
(Continued)

*Primary Examiner* — Stephen R Koziol
*Assistant Examiner* — Benedict E Lee
(74) *Attorney, Agent, or Firm* — Rimon P.C.

(57) ABSTRACT

An image processing using a plurality of specimen images obtained by successively applying a plurality of types of staining to a specimen to be evaluated and imaging the specimen after staining for at least two types of staining is performed. The image processing comprises: extracting an inner region corresponding to inward of a cell membrane of a single cell in the specimen based on at least one of the specimen images; specifying a cell region corresponding to an individual cell included in the specimen by expanding the inner region outwardly; and performing image cytometry for the cell region based on the specimen images. In analyzing a pathological specimen on a cell-by-cell basis, it is possible to deal with multiple immunostaining and specify the positions of individual cells and evaluate each cell separately even when a cell density in the specimen is high.

8 Claims, 8 Drawing Sheets (51) Int. Cl.
  *G01N 15/10*   (2024.01)
  *G01N 15/14*   (2024.01)
  *G01N 15/1429*   (2024.01)
  *G06T 7/187*   (2017.01)
  *G06T 7/30*   (2017.01)
  *G06V 10/22*   (2022.01)

(52) U.S. Cl.
  CPC ............... *G06T 7/30* (2017.01); *G06V 10/22* (2022.01); *G01N 15/01* (2024.01); *G01N 2015/1006* (2013.01); *G01N 2015/1497* (2013.01); *G06T 2207/10056* (2013.01); *G06T 2207/30024* (2013.01)

(58) Field of Classification Search
  CPC .......... G06T 2207/10056; G06T 2207/30024; G06T 7/0012; G06T 2207/10016; G06T 2207/10024; G06T 2207/10064; G06T 2207/20081; G06T 7/11; G01N 15/1429; G01N 2015/0065; G01N 2015/1006; G01N 2015/1497; G01N 33/4833; G01N 33/48375; G06V 10/22
  See application file for complete search history.

(56) References Cited

U.S. PATENT DOCUMENTS

| | | | |
|---|---|---|---|
| 8,600,142 B2 * | 12/2013 | Berndt | G01N 1/30 |
| | | | 382/128 |
| 9,224,193 B2 * | 12/2015 | Tsujimoto | G06T 5/50 |
| 9,934,571 B2 * | 4/2018 | Ozaki | G06T 7/60 |
| 10,890,576 B2 * | 1/2021 | Mimura | G06T 7/62 |
| 11,074,692 B2 * | 7/2021 | Sekiguchi | G06T 7/0014 |
| 11,222,415 B2 * | 1/2022 | Ozcan | G06T 5/70 |
| 11,436,718 B2 * | 9/2022 | Yoshida | G06F 18/2411 |
| 11,482,320 B2 * | 10/2022 | Klaiman | G06T 7/0012 |
| 11,842,556 B2 * | 12/2023 | Sekiguchi | G06V 20/698 |
| 2006/0257013 A1 | 11/2006 | Ramm et al. | |
| 2009/0297015 A1 | 12/2009 | Jetzek | |
| 2013/0108139 A1 | 5/2013 | Binnig et al. | |
| 2015/0125953 A1 * | 5/2015 | Hashino | C12N 5/062 |
| | | | 435/366 |
| 2015/0138334 A1 * | 5/2015 | Usuba | G06V 20/69 |
| | | | 382/134 |
| 2016/0216209 A1 | 7/2016 | Okada et al. | |
| 2017/0103521 A1 | 4/2017 | Chukka et al. | |
| 2017/0160171 A1 * | 6/2017 | Tsujikawa | G01N 1/44 |
| 2019/0042958 A1 | 2/2019 | Letterie et al. | |
| 2019/0064037 A1 | 2/2019 | Boyden et al. | |
| 2020/0090330 A1 * | 3/2020 | Chefd'hotel | G06N 3/045 |

FOREIGN PATENT DOCUMENTS

| | | | | |
|---|---|---|---|---|
| EP | 3 611 695 A1 | 2/2020 | | |
| JP | 2005-525550 A | 8/2005 | | |
| JP | 2013113818 A * | 6/2013 | | |
| JP | 2017068308 A * | 4/2017 | | |
| JP | 2019-509057 A | 4/2019 | | |
| JP | 2019-511914 A | 5/2019 | | |
| WO | 2015/045962 A1 | 4/2015 | | |
| WO | WO-2016076104 A1 * | 5/2016 | ............. | G01N 33/48 |
| WO | WO-2018198253 A1 * | 11/2018 | ............ | G01N 33/483 |
| WO | WO-2019188647 A1 * | 10/2019 | ............. | G01N 21/64 |
| WO | WO-2019225506 A1 * | 11/2019 | | |
| WO | WO-2020145605 A1 * | 7/2020 | ........... | G06T 3/4046 |

OTHER PUBLICATIONS

Denk et al. ("Serial block-face scanning electron microscopy to reconstruct three-dimensional tissue nanostructure." PLoS biology 2.11 (2004): e329.) (Year: 2004).*

Tleis et al. "Contour expansion algorithm preprocessed by hough transform and circular shortest path for ovoid objects." 2015 International Conference on Image Processing Theory, Tools and Applications (IPTA). IEEE, 2015. (Year: 2015).*

Guray Akturk: "Multiplexed Immunohistochemical Consecutive Staining on Single Slide (MICSSS): Multiplexed Chromogenic IHC Assay for High-Dimensional Tissue Analysis", Biomarkers for Immunotherapy of Cancer, Sep. 10, 2019 (Sep. 10, 2019), pp. 497-519.

Ortiz De Solorzano C et al., "Segmentation of nuclei and cells using membrane related protein markers", Journal of Microscopy, Blackwell Science, GB, vol. 201, No. 3, Mar. 1, 2001 (Mar. 1, 2001), pp. 404-415.

Ali Can et al., "Techniques for Cellular Quantitation of Cancer Biomarkers" In: "Analytical Chemistry", Jun. 1, 2018 (Jun. 1, 2018), American Chemical Society, vol. 89, pp. 1-29.

Extended European Search Report issued in corresponding European Patent Application No. 21189776.4-1210, dated Jan. 26, 2022.

Notice of Reasons for Refusal received in corresponding Japanese Patent Application No. 2020-141765, dated Apr. 2, 2024.

* cited by examiner

WITHOUT REGISTRATION

WITH REGISTRATION

SPECIMEN ANALYSIS METHOD AND IMAGE PROCESSING METHOD

CROSS REFERENCE TO RELATED APPLICATION

The disclosure of Japanese Patent Application No. 2020-141765 filed or Aug. 25, 2020 including specification, drawings and claims is incorporated herein by reference in its entirety.

BACKGROUND OF THE INVENTION

1. Field of the Invention

This invention relates to a method for analyzing a specimen image captured by imaging a pathological specimen on a cell-by-cell basis and an image processing method for assisting the former method, particularly to an analysis using an immunohistochemical technique.

2. Description of the Related Art

In the field of recent immunohistochemistry, a so-called single cell analysis not only seeing a specimen as a group of cells, but also focused on individual cells constituting the specimen is attracting attention. This is a method for measuring expression levels, positions and the like of biological materials such as proteins and protein-related materials on a cell-by-cell basis. A flow cytometry technique is known as a typical analysis technique of this approach. This technique is for causing a fluid containing cells dispersed therein to flow in a narrow flow passage and successively measuring the cells passing one by one in the flow passage.

This flow cytometry technique has a problem that the position information of cells in a specimen is lost. Thus, a technique is considered which directly measures, from an image captured by imaging a tissue section, individual cells using an image processing technique. For instance, in a technique described in WO 2015/045962 (patent literature 1), staining enabling bright field observation and staining for producing fluorescence ate respectively applied to different biological materials in the same specimen. The expression position of a biological material as an observation object is specified by the comparison of a bright field image and a fluorescent image obtained by imaging this specimen, and the expression level thereof is specified from a measurement result of a fluorescence amount.

With the conventional technique described in patent literature 1 described above, the expression position and the expression level of a specific biological material can be detected with high accuracy. However, there is the following problem to be solved. That is, a method for specifying the positions of the biological materials is not described in detail in patent literature 1, but it is possibly difficult to clearly separate individual cells in a specimen in which the cells exist at a high density. Recently, a plurality of types of staining have been applied to the same specimen and a plurality of types of biological materials have been measured with improvement in multiplexed immunohistochemistry. However, since the above conventional technique has constraint conditions for staining methods, this technique cannot be immediately applied to such a multiple immunostained specimen.

Specifically, then is the following problem. A tissue section having a thickness of 4 μm or more is generally used as a specimen for multiplexed immunohistochemistry. In such a tissue section, it is difficult to separate individual cells in an image since the cells overlap also in a depth direction. This problem is particularly prominent in a specimen having a high cell density. If the tissue section is thinned, it is advantageous in terms of cell discrimination, but the number of times of staining is limited due to another problem that the specimen is easily damaged.

SUMMARY OF THE INVENTION

This invention was developed in view of the above problem and an object thereof is to provide a technique, in analyzing a pathological specimen on a cell-by-cell basis, capable of dealing with multiple immunostaining and specifying and measuring the positions of individual cells also when a cell density in the specimen is high.

To achieve the above object, one aspect of this invention is directed to a specimen analysis method. The specimen analysis method includes obtaining a plurality of specimen images by successively applying a plurality of types of staining to a specimen to be evaluated and imaging the specimen after staining for at least two types of staining, extracting an inner region corresponding to inward of a cell membrane of a cell in the specimen based on at least one of the specimen images, specifying a cell region corresponding to an individual cell included in the specimen by expanding the inner region outwardly, and performing image cytometry for the cell region based on the specimen images.

Further, another aspect of this invention is directed to an image processing method using a plurality of specimen images obtained by successively applying a plurality of types of staining to a specimen to be evaluated and imaging the stained specimen for at least two types of staining. To achieve the above object, the image processing method includes extracting an inner region corresponding to inward of a cell membrane of a cell in the specimen based on at least one of the specimen images, specifying a cell region corresponding to an individual cell included in the specimen by expanding the inner region outwardly, and performing image cytometry for the cell region based on the specimen images.

In these aspects of the invention, the "image cytometry" indicates an image processing for measuring at least one of pieces of quantitative information such as the shapes, sizes of the cells in the specimen, expression levels of biological materials (e.g. proteins) in the cells and the like on a cell-by cell basis based on image data of the specimen images.

In the invention thus configured, the regions inward of (in other words, surrounded by) the cell membranes, out of the cells appearing in the specimen image, are extracted. Even if a plurality of the cells are in contact, the regions inward of the cell membranes are isolated from each other among the cells. Accordingly, even the cells in contact with each other via the cell membranes can be discriminated as individual cells. That is, in this stage, the positions, number and the like of the individual cells in the specimen can be grasped. Moreover, the cell regions are determined by expanding the inner regions. By so doing, the positions occupied in the image by the cells including up to the cell membranes can be individually determined.

When many cells exist at a high density, boundaries between those cells tend to be ambiguous. Particularly, when it is tried to extract cell regions as structures including up to cell membranes, a plurality of cells may be integrally extruded as one cell due to the unclearness of the boundaries. In view of this, in the invention, the inner regions inward of the cell membranes are first extracted from the specimen image and the cell regions corresponding to the individual cells are specified by expanding the extracted inner regions outwardly. Therefore, even if a tissue has a high cell density, individual cells constituting the tissue can be precisely extracted.

If the regions occupied by the individual cells in the specimen image are specified in this way, an image cytometry technique, which is an image processing technique for extracting quantitative information of each cell in an image, can be applied. In this way, the cells constituting the tissue specimen can be individually analyzed and the individual pieces of quantitative information can be obtained.

As described above, in the invention, a plurality of specimen images are obtained by staining a specimen by a plurality of types of staining methods and performing imaging a plurality of times in that process. Inner regions inward of cell membranes are first specified from at least one of those specimen images, and cell regions are determined by expanding the inner regions outward. Thus, even if the specimen has a high cell density, the individual cells can be precisely discriminated. Further, multiple immunostained specimens can also be dealt with.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

Hereinafter, a specimen analysis process (hereinafter, merely referred to as an "analysis process"), which is one embodiment of a specimen analysis method according to the invention, is described. This analysis process is a process for specifying the positions of individual cells from an image of a specimen including a multitude of cells such as a pathological tissue specimen and obtaining quantitative information such as expression states and expression levels of biological materials in each cell. A basic technical concept of this process follows a multiple immunostaining technique and is not described since a basic principle of multiple immunostaining is known. First, this analysis process is summarized with reference to FIG. 1 and, then, the content of each processing step is described in detail.

Figure 1:
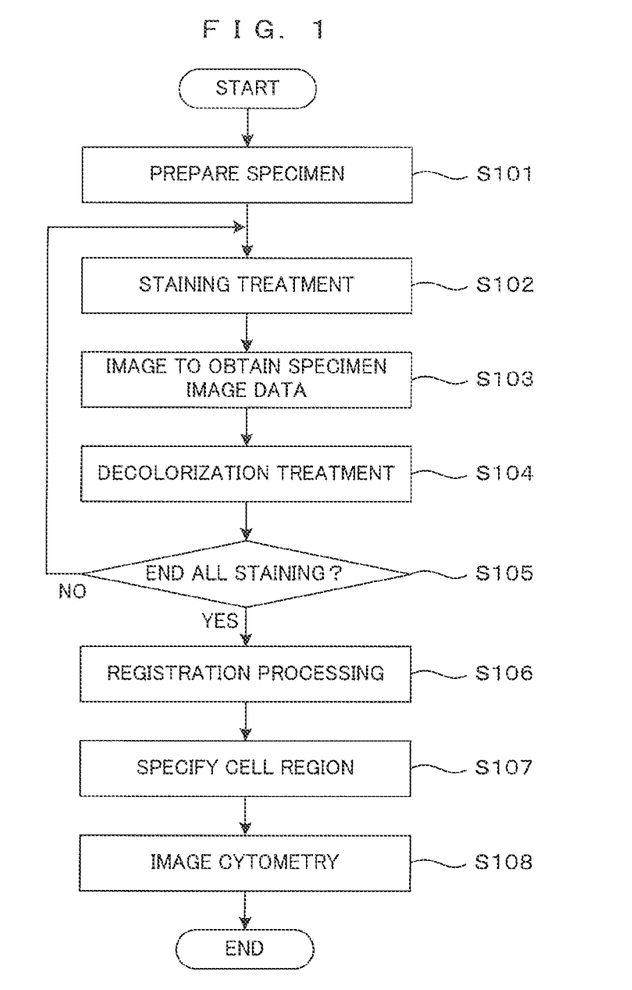
FIG. 1 is a flow chart showing a flow of the specimen analysis process of this embodiment.

FIG. 1 is a flow chart showing a flow of the specimen analysis process of this embodiment. First, a pathological tissue specimen to be analyzed is prepared (Step S101). For example, the specimen can be prepared by fixing a tissue section on a slide glass.

For the thus prepared specimen, a staining treatment by a staining method for a purpose (Step S102), the acquisition of specimen image data by imaging the stained specimen (Step S103) and a decolonization treatment (Step S104) are repeated in this order a plurality of times. More specifically, every time the specimen is stained, the specimen is imaged by an imaging method to be described later and the captured image is digitized as specimen image data. The specimen after imaging is decolorized in preparation for the next staining. The above process is repeated until imaging is finished in all types of staining methods prepared in advance (Step S105). In this way, a plurality of pieces of specimen image data corresponding to a plurality of specimen images having mutually different stained states are obtained for the same specimen.

Decolorization and staining operations are performed between imaging times for the plurality of specimen images obtained by such imaging. Thus, the position of the specimen may be shifted in image frames even if imaging is performed by the same imaging apparatus. To correct such shifts for the alignment of the respective images, a registration processing is performed (Step S106).

Using the plurality of specimen images having mutual position shifts corrected, a cell region extraction processing for specifying a region occupied by each of the individual cells in the specimen is performed (Step S107). In this way, the position of each cell in the specimen image and the region occupied thereby are specified. As a result, even if a multitude of cells exist at a high density in the specimen, those cells are respectively recognized as separate cells.

A quantitative analysis by image cytometry is performed for the specified individual cells (Step S108). In this way, the quantitative information such as the states and expression levels of the biological materials expressed in each cell is obtained for each cell. The obtained information is statistically processed if necessary and provided for evaluation by a user (clinician, researcher or the like). Various image cytometry techniques have been put to practical use. Since the image cytometry technique appropriately selected from those for a purpose can be applied also in this embodiment, the content of image cytometry is not described in detail.

Out of the above processing steps. Steps S106 to S108 can be, for example, performed as image processings by a computer device. In this sense, the invention can be carried out with these steps as a program to be executed by the computer device or as a storage medium non-transiently storing these steps.

Next, more detailed processing contents of the respective processing steps in the above analysis process are successively described. First, a generally adopted method can be applied for the preparation of the specimen in Step S101. However, for the purpose of separating the cells in the specimen image one by one, the tissue section serving as the specimen is desirably constituted by a single layer of cells. That is, a thickness of the specimen is preferably equal to or smaller than thicknesses of the cells constituting this tissue. Specifically, a section thinner than 4 μm, which is a general thickness as a tissue specimen used in immunohistochemical analysis, is desirable and the thickness can be, for example, 2 μm or less. By using a thin tissue section, the overlap of cells in a thickness direction of the specimen decreases. In this way, the clearness of membrane staining, cytoplasmic staining and nuclear staining can be improved and accuracy in specifying cell regions can be improved. This thinning of the specimen is advantageous in recognizing the cells. On the other hand, since the specimen becomes easily damaged and the number of times of staining cannot be increased, this thinning is disadvantageous for multiple staining. Thus, staining is desirably performed a minimum number of times required for a targeted analysis.

For the staining treatment of Step S102, a staining method can be selected for a purpose from various staining methods put to practical use. For the purpose, of performing an immunohistochemical analysis, at least one type of staining method utilizing an antigen-antibody reaction is preferably included. For instance, proteins (membrane-localized proteins, nucleus-localized proteins, cytoplasm-localized proteins, etc.) effective to classify the types and functions of the cells can be stained according to the purpose of the analysis. In a recently actively researched immune-related area, membrane-localized proteins are often used to classify the types and degrees of maturity of cells. Further, in terms of accurately specifying cell regions, the staining of membrane-localized proteins or cytoplasm-localized proteins is preferably included.

Further, as described later, inner regions, which are regions inward of cell membranes in the cells in the specimen image, are extracted in this embodiment. To this end, it is desirable to include at least one of a staining method for selectively staining biological materials inward of the cell membranes and a staining method for selectively staining only the cell membranes. Cell nuclei, cytoplasms and the like can be, for example, utilized as biological materials inside the cell membranes. For this, a staining method for selectively staining cell nuclei and/or cytoplasms is desirably included. Further, a hematoxylin eosin (HE) staining method, which is a general staining method for observing bright field cells, or its alternative staining method may be included for visual observation by a user. Since HE staining can stain cell nuclei and cytoplasms respectively in blue and red, this is effective for the extraction of the inner regions described above.

If the type of the cells to be analyzed is determined in advance, it is effective to stain proteins confirmed to be expressed or expected to be expressed in those cells. For example, the staining of LCA (leukocyte common antigen) protein is effective for the analysis of immune cells. Further, the staining of cytokeratin is effective for the analysis of epithelial tumor cells.

By performing multiple immunostaining in which immunostaining for a plurality of antigens are combined, a plurality of types of biological materials can be respectively individually visualized. For example, multiple immunostaining is suitable for the purpose of examining the colocalization of those biological materials. The followings are known as staining methods applicable to such multiple immunostaining and these can be appropriately combined and utilized. For example, in the study of tumor immunity, immunostaining for CD3, CD4, CD8, CD20 and CD79a and antigens/proteins, such as PD-1, functioning as immune mechanisms are used. The types and states of T-cells and B-cells are analyzed by those informations, viz., positive/negative combinations. In these immunostainings, all the cells are not equally and ideally stained. Thus, by using a plurality of immunostained images in combination, accuracy in specifying cell regions can be improved.

In Step S103, the stained specimen is converted into digital data by imaging. Note that imaging is performed for each staining in the process shown in FIG. 1. However, a case where one imaging is performed after a plurality of types of staining are successively performed for a purpose may be included. Specifically, imaging can be performed as follows.

Figure 2A:
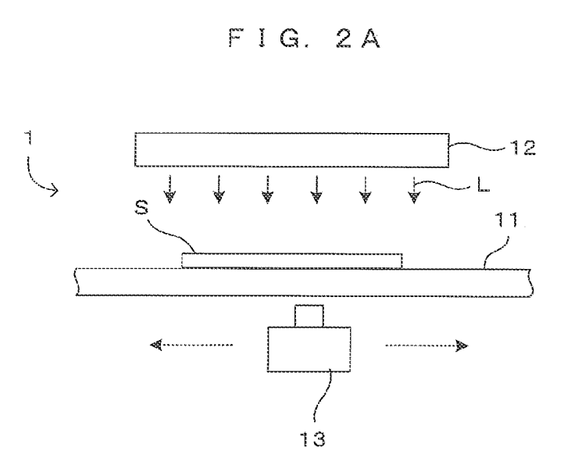
FIGS. 2A and 2B are diagrams showing an example of the specimen imaging method.
Figure 2B:
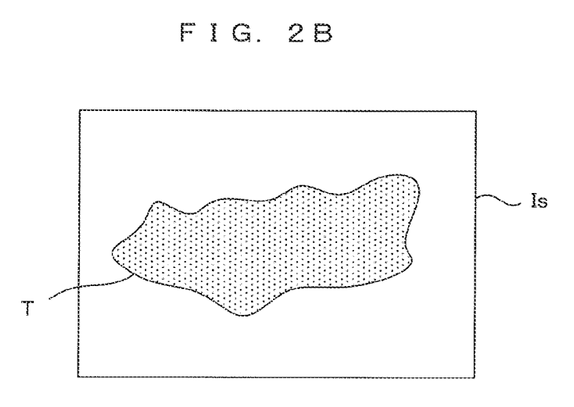

FIGS. 2A and 2B are diagrams showing an example of the specimen imaging method. FIG. 2A shows a main configuration example of an imaging apparatus 1 for realizing imaging. For example, a specimen S prepared on a slide glass is supported in a substantially horizontal posture by appropriate supporting means such as a contact glass 11. An illumination light source 12 is arranged above the specimen S and irradiates substantially uniform illumination L to be incident on the specimen S. Bright field imaging can be performed if the illumination light L is visible light, and fluorescence imaging can be performed it the illumination light L is excitation light for fluorescent substances.

An imago scanner 13 is arranged below the specimen S supported by the contact glass 11. The image scanner 13 includes a linear image sensor (not shown) having a longitudinal direction perpendicular to the plane of FIG. 2A. As shown by dotted-line arrows, the image scanner 13 is moved in the directions orthogonal to the longitudinal direction, i.e. lateral directions of the plane of FIG. 2A to scan the specimen S. In this way, digital image data corresponding to a two-dimensional image of the specimen S is obtained. Imaging may be performed using a two-dimensional image sensor.

FIG. 2B shows an example of a specimen image. As illustrated in FIG. 2B, a specimen image Is is so imaged that a tissue section T in the specimen is entirely accommodated in a field of view. Such an image may be called a whole slide image. A large tissue section T may be imaged while being divided into a plurality of images. An imaging resolution is desirably sufficiently smaller than the size of cells. In this sense, the principle of an imaging apparatus for imaging by causing a linear image scanner with a high resolution to scan with respect to the specimen S is effective. The obtained image is desirably made presentable to the user at various display magnifications.

In Step S104, the specimen after imaging is decolorized. By so doing, the influence of the previous staining can be eliminated prior to new staining. For example, a staining result can be individually obtained, for example, for each of biological materials colored by two types or staining methods. Further, for example, a plurality of types of biological materials colored by one type of staining method can be discriminated using a result of another staining method. Note that if the influence of the previous staining is not problematic, the next staining may be performed without decolorization.

Multiple immunostaining is a technique for visualizing a plurality of types of biological materials on one image by overlapping a plurality of types of staining results on the specimen. By decolorization, such an overlapping effect is not obtained, but the specimen in each stained state is imaged and saved as specimen image data. Thus, by synthesizing those specimen images by an image processing, effects of multiple immunostaining can be realized in a pseudo manner. Rather, since the images in arbitrary stained states can be selected and overlapped regardless of a staining order, it is also possible to generate such a pseudo-stained image that cannot be realized by single-time multiple immunostaining on the specimen.

Since each specimen image is captured while staining and decolorization are repeated, the positions of the tissue section T may be shifted from each other between the images, such as due to the variation of the set position of the specimen S during imaging. To deal with this problem, the alignment (registration) of the specimen images obtained by each imaging is performed in Step S106. The registration is performed, utilizing points corresponding to each other among the respective specimen images.

Figure 3:
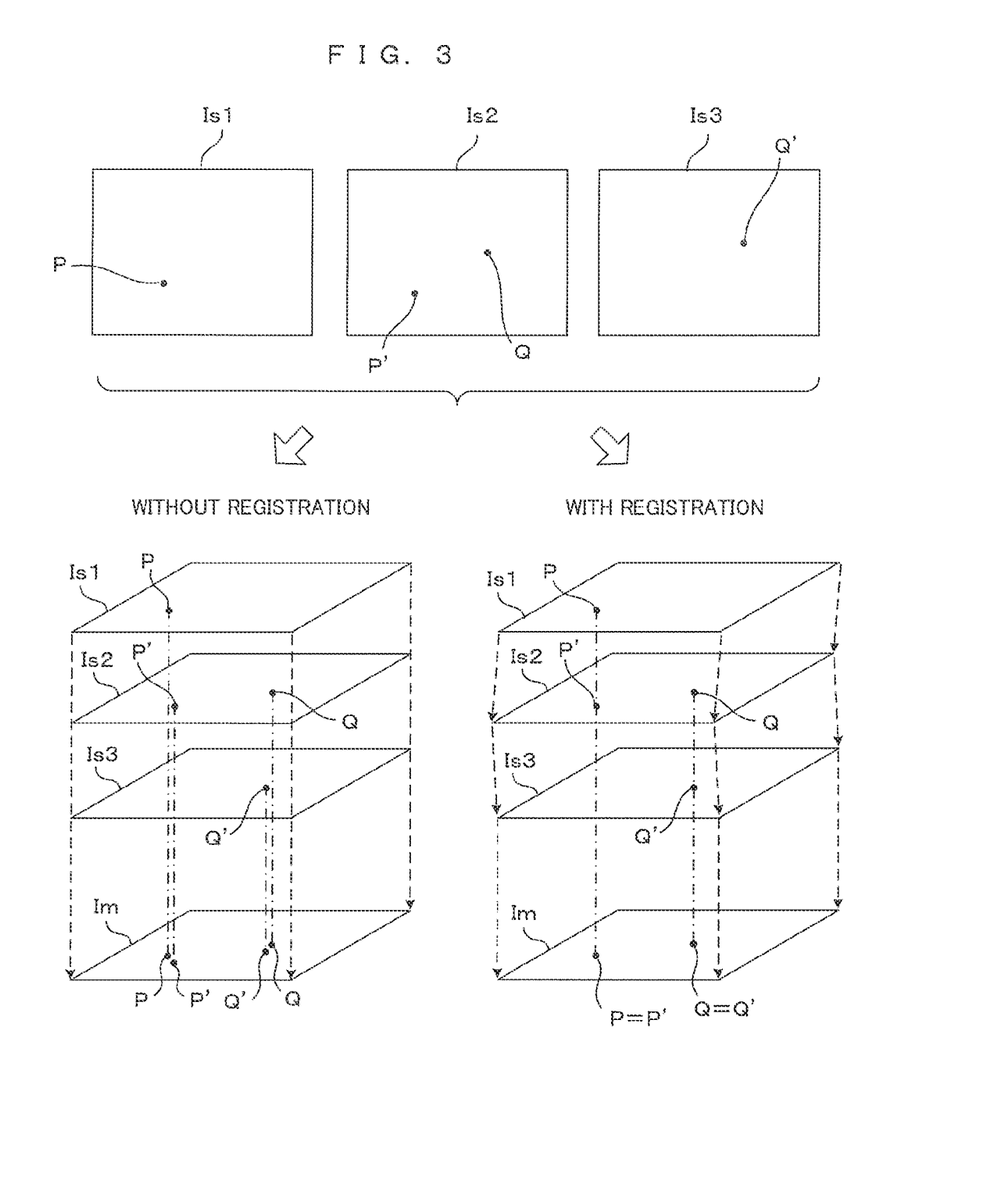
FIG. 3 is a diagram showing the principle of the registration processing.

FIG. 3 is a diagram showing the principle of the registration processing. Here, registration among three specimen images Is1 to Is3 obtained from the same specimen by mutually different staining methods is described as an example. Points corresponding to each other between the specimen images Is1 and Is2 are denoted by P and P'. Here, the "points corresponding to each other" mean that one point in one image and one point in another image are in such a relationship as to indicate the same position on the specimen S. Similarly, points corresponding to each other between the specimen images Is2 and Is3 are denoted by Q and Q'.

The specimen images Is1 to Is3 are obtained by different staining methods. Thus, it is possible that biological materials visualized in one image are not visualized in the other images and are difficult to discriminate these from the images. This is, for example, a case where no point corresponding to the point Q appears in the specimen image Is1 and no point corresponding to the point P appears in the specimen image Is3. However, as illustrated below, if each specimen image has a point corresponding to a point in at least one other specimen image, images in which no corresponding point is found out can be indirectly corrected by performing a position correction in each of those images.

In a case example of FIG. 3, the point P in the specimen image Is1 and the point P' in the specimen image Is2 correspond to each other. Further, the point Q in the specimen image Is2 and the point Q' in the specimen image Is3 correspond to ouch other. It these specimen images Is1 to Is3 are overlapped without registration, the positions of the points are possibly different at least either between the points P and P' or between the points Q and Q' in a synthetic image Im due to the position shift during imaging described above as shown in a left-lower part of FIG. 3. Such a position shift possibly becomes an error factor in specifying the positions of the individual cells from the specimen image.

Accordingly, as shown in a right-lower pan of FIG. 3, the specimen images Is1 to Is3 are synthesized after the positions of the images are so corrected that the points P, P' overlap each other between the specimen images Is1 and Is2 and the points Q, Q' overlap each other between the specimen images Is2 and Is3. Then, on the synthetic image Im, the points P and P' coincide and the points Q and Q' coincide. In this way, the error factor in specifying the positions of the individual cells can be comprehensively eliminated from the plurality of specimen images. A method for obtaining position coordinates of points corresponding to each other in a plurality of specimen images for each specimen image and shifting relative positions between the images according to differences of those coordinates can be used as a specific correction method. Further, a method using pixel information of entire images, e.g. a method for obtaining relative positions, which make differences between pixel values at the same position small or a method for obtaining relative positions, which maximize correlation values of pixels, can also be used without using the position coordinates of the corresponding points. The above is the principle of an example of the registration processing. However, a content of the registration processing is not limited to this.

Subsequently, the cell region extraction processing of Step S107 is described with reference to FIGS. 4 to 8B. The shapes and sizes of cells in a specimen have large individual differences and a multitude of cells adhere to each other in many cases. The extraction processing of this embodiment described below enables the individual cells to be precisely extracted also in such a specimen.

Figure 4:
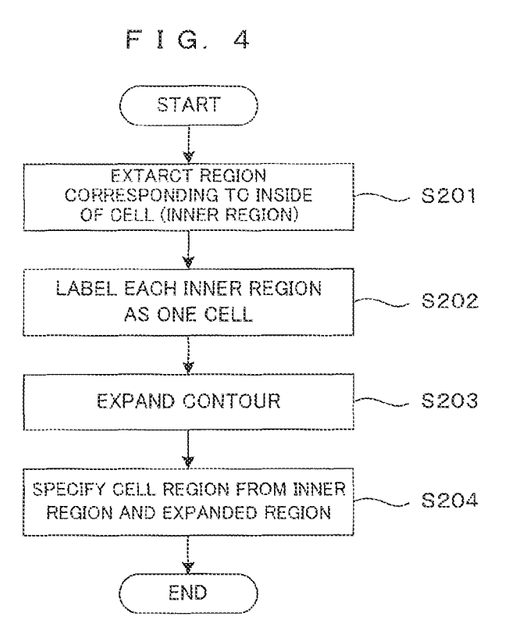
FIG. 4 is a flow chart showing the cell region extraction processing.
Figure 5A:
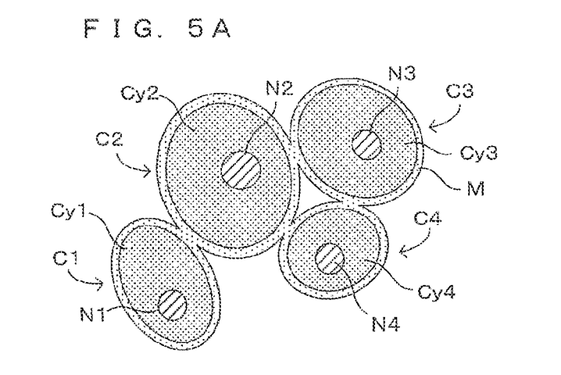
FIGS. 5A to 5D are diagrams schematically showing image changes in this processing process.

FIG. 4 is a flow chart showing the cell region extraction processing. Further. FIGS. 5A to 6B are diagrams schematically showing image changes in this processing process. FIG. 5A schematically shows an example of an image in which a plurality of cells adhere to each other. Here, four cells C1 to C4 are in contact with each other. Each of the cells C1 to C4 includes a nucleus (cell nucleus) N1 to N4 inside. Each cell C1 to C4 is surrounded by a cell membrane M. If the cell membranes M are in contact with each other, boundaries thereof may become unclear. A cytoplasm Cy1 to Cy4 is present between the cell nucleus N1 to N4 and the cell membrane M. Although not shown, various organelles (mitochondria, Golgi bodies, etc.) and various biological materials such as cytosols and vacuoles are possibly included in the cytoplasms Cy1 to Cy4.

The individual cells need to be separated and discriminated from such a group of the cells. To enable this, regions corresponding to the insides of the cells (called "inner regions" in this specification) in the specimen image are first extracted, using at least one of the plurality of specimen images having different staining methods applied thereto (Step S201). More specifically, the regions inward of the cell membranes M in the cells are the inner regions. For example, if there is a specimen image, to which a staining method for selectively staining biological materials present only inward of cell membranes was, for example, applied, such a specimen image can be used. Further, an image in which only cell membranes are selectively stained can be, for example, used as a specimen image. This is because closed regions surrounded by the cell membranes can be regarded as the inner regions in such images.

Further, a plurality of specimen images having different stained states may be used in the extraction of the inner regions. For example, it two or more types of biological materials are stained by one type of staining method, it may not be possible to extract desired biological materials only from such a specimen image. By combining a plurality of specimen images having different stained states, such a problem can be solved in some cases. Specifically, the inner regions can be extracted, for example, by combining a specimen image in which cell nuclei are stained and a specimen image in which cytoplasms are stained. Further, for example, regions each surrounded by a cell membrane and including a cell nuclei inside can be extracted as the inner regions from a specimen image in which only the cell membranes are stained and a specimen image in which the cell nuclei are stained.

Further, arbitrary ones of various biological materials present inward of the cell membranes in cells can be used as extraction objects. For example, any selected from the cell nuclei and cytoplasms such as cytosols, mitochondria and Golgi bodies can be used. For accurate extraction, it is desirable to select biological materials having a property of being selectively stained by a certain type of staining method. For example, since various methods for selectively staining only cell nuclei are established, the cell nuclei are biological materials suitable for such a purpose.

Note that biological materials to be included in the inner regions may not necessarily be of one type. For example, in a specimen image in which two or more types of biological materials are simultaneously expressed, if both biological materials are apparently present in cells, those biological materials need not be distinguished. That is, the plurality of types of biological materials may be both utilized for the extraction of the inner regions without being distinguished.

Figure 5B:
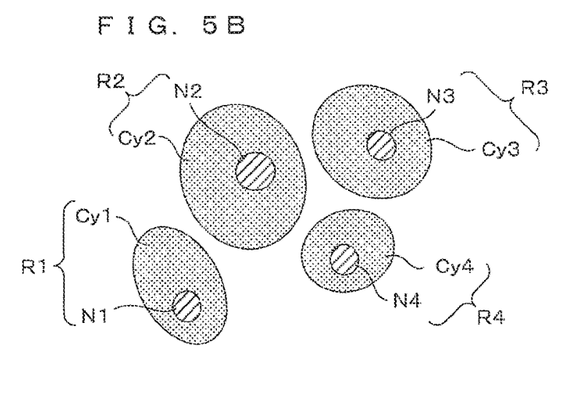

FIG. 5B schematically shows an extraction result of the cell nuclei N1 to N4 and regions corresponding to the cytoplasms Cy1 to Cy4 around the cell nuclei N1 to N4. Here, a total region of the cell nucleus N1 and the cytoplasm Cy1 around the cell nucleus N1 can be regarded as an "inner region" R1 of one cell C1. Similarly, a total region of the cell nucleus N2 and the cytoplasm Cy2 around the cell nucleus N2, a total region of the cell nucleus N3 and the cytoplasm Cy3 around the cell nucleus N3 and a total region of the cell nucleus N4 and the cytoplasm Cy4 around the cell nucleus N4 are respectively equivalent to "inner regions" R2 to R4 of the cells C2 to C4.

Figure 5C:
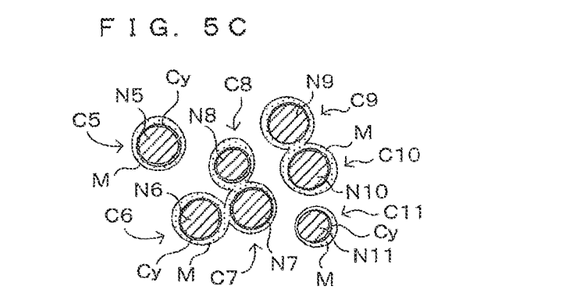
Figure 5D:
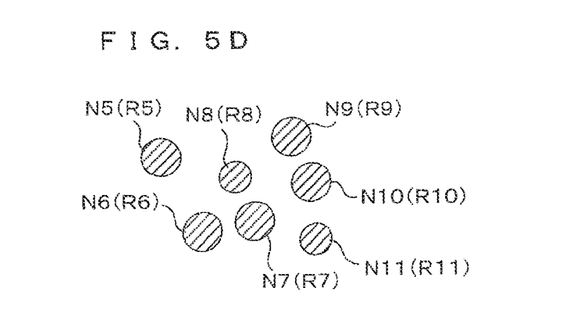

FIG. 5C schematically shows a structure example of small cells such as lymphocytes. In small-sized cells C5 to C11 such as lymphocytes, which are suitable as analysis objects for which multiple immunostaining is effective, there are cases where the cytoplasms Cy are poor and regions inside cell membranes can be regarded as being substantially occupied by cell nuclei N5 to N11. In such cases, even if regions occupied by the cell nuclei N5 to N11 in a specimen image are regarded in "inner regions", no large error is thought to be caused. That is, as shown in FIG. 5D, the regions of the cell nuclei N5 to N11 extracted from the image can be directly handled as inner regions R5 to R11. Therefore, it is also possible to extract the inner regions from the specimen image in which the cell nuclei are selectively stained.

The inner regions R1 to R4 (or inner regions R5 to R11) extracted in this way do not include regions of surrounding cell membranes M. Thus, even if the cells are in contact via the cell membranes M in the specimen, the inner regions are isolated from each other. That is, the inner regions R1 to R4 (R5 to R11) correspond one-to-one to the cells C1 to C4 (C5 to C11). By such a correspondence, the cells C1 to C4 (C5 to C11) even in an adhering state are recognized as mutually separate cells. Thereafter, the individual cells C1 to C4 (C5 to C11) can be individually handled. Accordingly, labelling is performed to distinguish the respective specified inner regions C1 to C4 (C5 to C11) (Step S202). This labelling can also be finally utilized to distinguish the individual cells C1 to C4 (C5 to C11) in the analysis process on a single-cell basis.

Figure 6A:
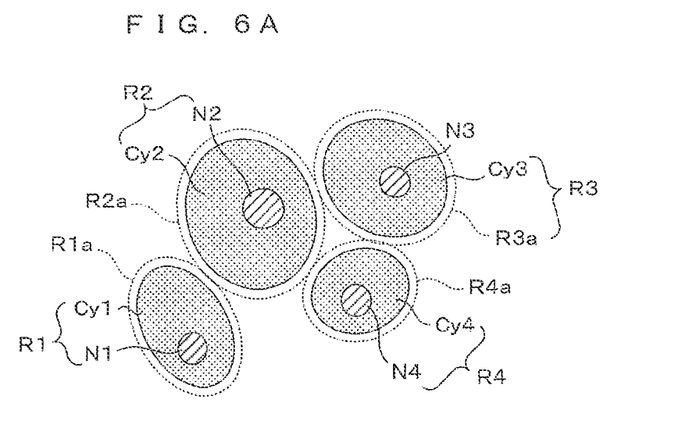
FIGS. 6A and 6B are diagrams schematically showing image changes in this processing process.
Figure 6B:
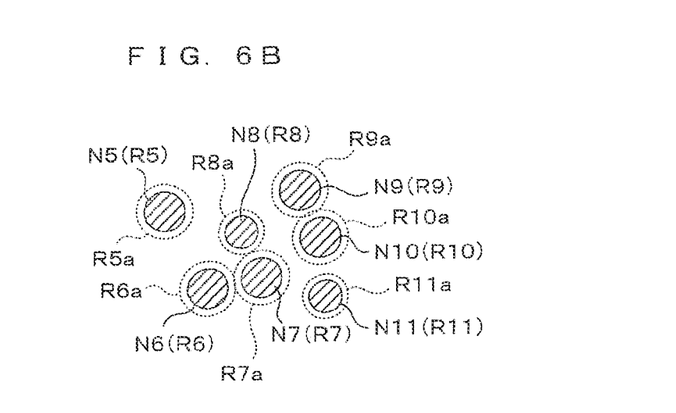

The inner region R1 to R4 (R5 to R11) indicates the inclusion of at least this region in the cell, but does not indicate the outer edge of the cell including the cell membrane M. In this embodiment, an imaging processing is performed which outwardly expands the contours of the inner regions R1 to R4 (R5 to R11) already separated from each other (Step S203). FIG. 6A schematically shows a result or the expansion processing based on an extraction result of FIG 5B, and FIG. 6B shows a result of the expansion processing based on an extraction result of FIG. 5D. Dotted lines show examples of the contours after the expansion. The regions after the expansion, i.e. total regions of the original inner regions and expanded regions thereof, are finally specified as cell regions corresponding to the individual cells C1 to C4 (C5 to C11) (Step S204).

Figure 7A:
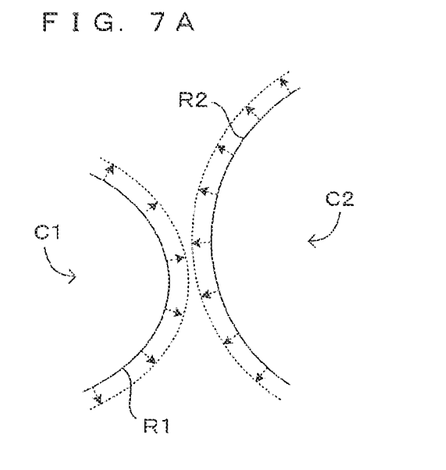
FIGS. 7A and 7B are diagrams schematically showing a processing of expanding the inner regions.
Figure 7B:
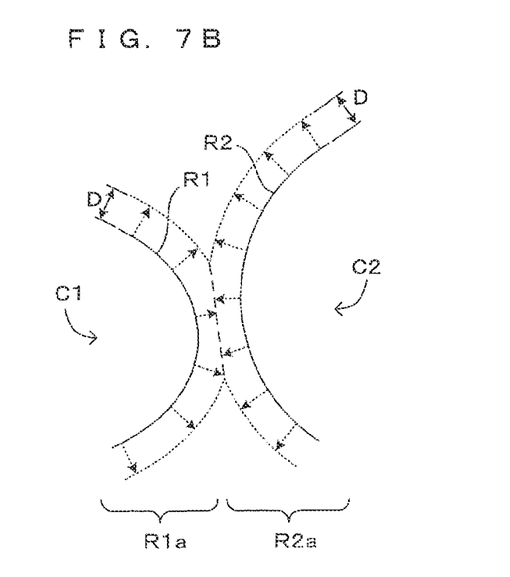

FIGS. 7A and 7B are diagrams schematically showing a processing of expanding the inner regions. Here, the expansion processing of the inner regions R1, R2 near a contact point of two cells C1, C2 is described as on example. As shown by arrows in FIG. 7A, contour parts equivalent to the outer edges of the inner regions R1, R2 are expanded outward by a predetermined amount (e.g. by one pixel). In this way, the inner regions R1, R2 are expanded by the predetermined amount toward regions corresponding to the cell membranes M surrounding these inner regions R1, R2. Dotted lines in FIG. 7A indicate the contours after the inner regions R1, R2 are expanded.

As shown in FIG 7B, such a contour expansion is performed until a width (expansion width) D of the expanded parts reaches a specified value determined in advance or until the contours after the expansion contact the other (expanded) inner regions. The specified value for the expansion width D can be set in advance as a value corresponding to a possible standard thickness for the cell membranes of the cells. In the case of extracting only the region of the cell nucleus as the inner region as shown in FIG. 5D, the sum of standard thicknesses of the cytoplasm and the cell membrane around the cell nucleus can be set as the specified value.

By so doing, the inner region R1a after the expansion is the sum of the original inner region R1 and a region surrounding the inner region R1 and having a predetermined width, and substantially coincides with a region occupied by the individual cell including the cell membrane M. Also in a part where two cells are in contact, a boundary is defined at an intermediate position between the both cells as shown by a broken line in FIG. 7B.

By performing the expansion processing in this way, the region R1a to R4a (R5a to R11a) substantially coinciding with a region occupied by each cell C1 to C4 (C5 to C11) in the specimen image can be specified for each cell as shown in FIG. 6A (FIG. 6B). In this sense, the inner region R1a to R11a after the expansion represents the region occupied by each cell C1 to C11 in the image, i.e. the cell region. If the adjacent cell regions are in contact with each other, those are distinguished as separate ones. If the regions corresponding to the cell regions are cut out from the original image, the cells C1 to C4 (C5 to C11) can be cut out from the image. In this way, the contours of the individual cells are properly defined while the individual cells are clearly distinguished.

In this method, by determining a specified value for the expansion amount based on the thicknesses of the cell membranes in the isolated cells, the regions occupied by the cells can be properly specified also for the isolated cells. Further, if a multitude of cells are apparently in contact in a specimen, a specified value may be determined based on thicknesses of cell membranes in such a case.

By specifying the cell region occupied by each cell in this way, each cell can be individually measured and the quantitative information thereof can be individually obtained even if a plurality of cells exist at a high density. That is, by performing the image cytometry with the individual cell regions as objects (Step S108 of FIG. 1), various pieces of information such as the position, size and shape of each cell and the expression state and expression level of each biological material can be obtained. In this embodiment, the content of the image cytometry and the types of pieces of information obtained thereby are not particularly limited. The result of the image cytometry can be utilized, for example, in presenting the stainability of immunostaining and in judging positive or negative state of the biological material characterizing specific diseases.

For the purpose of extracting the inner regions from the specimen image and analyzing each cell having the cell region specified therefor, a pre-trained machine learning model constructed by machine learning can be utilized. Since individual differences among cells are large in a specimen including a multitude of cells, it may be difficult to extract the individual cells by a simple threshold value processing, pattern matching or the like. If a learning model constructed by property performing machine learning based on morphological features of cells is used, an analysis process capable of flexibly dealing with such individual differences can be realized.

Figure 8A:
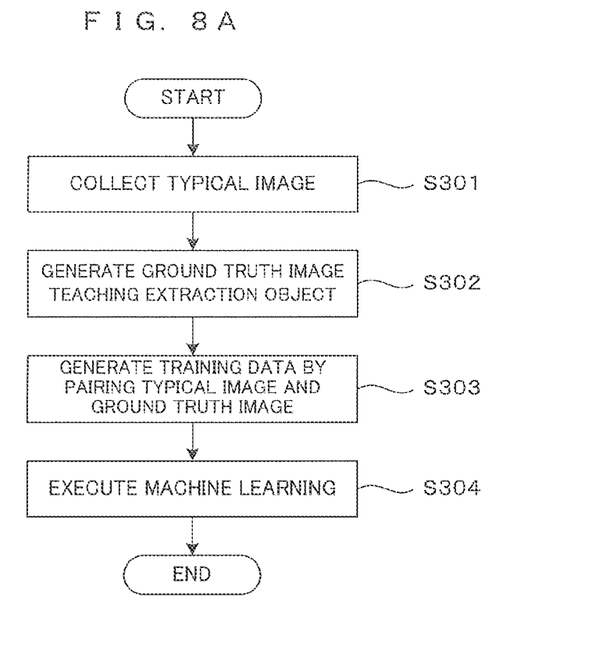
FIGS. 8A and 8B show an example of a machine learning model utilizable in this embodiment.
Figure 8B:
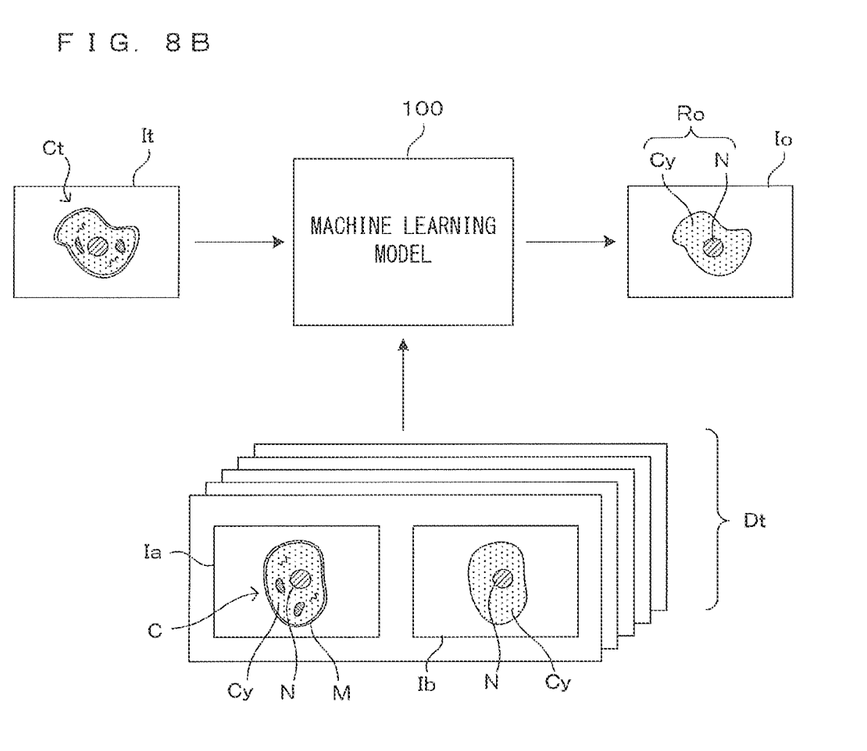

FIGS. 8A and 8B show an example of a machine learning model utilizable in this embodiment. Here, the construction of a learning model utilizable in extracting inner regions corresponding to total regions of cell nuclei and cytoplasms from a specimen image is described as an example. However, a similar method can be applied, such as when extraction objects are other biological materials or for the purpose of detecting and measuring desired biological materials from each cell after cell region specification.

FIG. 8A is a flow chart showing a process of constructing the learning model, and FIG. 8B is a diagram schematically showing the learning model. First, a multitude of typical images Ia, which become teachers in machine learning, are collected by a user (Step S301) and ground truth images Ib corresponding to the typical images Ia are prepared (Step S302). The ground truth image Ib is an image for teaching regions occupied by biological materials as extraction objects in the typical image Ia. For the purpose of extracting an inner region inward of a cell membrane from an image of a cell, various stained images by staining such as membrane staining, cytoplasmic staining and nuclear staining ate suitable as the typical images Ia, and images clearly showing the inner regions corresponding to the stained images as the extraction objects are suitable as the ground truth images Ib. The ground truth image Ib is prepared for each of the collected typical images Ia, and training data Dt is generated by pairing the typical images Ia and the corresponding ground truth images Ib (Step S303).

The training data Dt is given to a machine learning model 100 having an appropriate learning algorithm, and the machine learning model 100 performs machine learning (Step S304). Various machine learning models have been proposed, and an appropriate one can be selected from those and applied also in this embodiment. To construct a highly versatile learning model compatible with various cells and biological materials, a deep learning algorithm can be, for example, suitably utilized.

The machine learning model 100 constructed in this way has the following function. Specifically, if a test image It including a cell is given as an input image to the machine learning model 100, the machine learning model 100 outputs an output image Io representing a region inward of a cell membrane, i.e., only an inner region Ro, out of a cell Ct in the test image It. That is, the machine learning model 100 has a function of extracting only the inner region Ro from the unknown test image It. By giving suitable training data corresponding to a desired extraction object, the machine learning model 100 has a function of extracting various biological materials from a test image.

In this embodiment using a plurality of specimen images having different stained states, the region extraction using the pre-trained machine learning model as described above may be performed for the individual specimen images. Further, the region extraction using the machine learning model may be performed for an image obtained by synthesizing a plurality of specimen images. Even in the case of performing the region extraction using a synthetic image, this region extraction can be said to be an "extraction based on original specimen images" in that information of each of the original specimen images is utilized.

As described above, in this embodiment, it plurality of typos of staining are successively applied to the specimen S to be evaluated and the specimen S is imaged every time.

Then, the inner regions inward of the cell membranes are extracted based on at least one of those specimen images, e.g. the specimen image in which the cell nuclei, the cytoplasms or the cell membranes are stained. The inner regions extracted in this way do not include the regions of the cell membranes. Thus, even if the cells are in contact with each other, the inner regions extracted from the individual cells are isolated from each other. In other words, each of the extracted inner regions represents the presence of one cell. In this way, even if the individual cells are in contact with each other in the specimen, those cells are individually discriminated.

By expanding the inner regions outward, the regions of the cell membranes surrounding the inner regions can be included. The expansion amount is set according to the possible thicknesses of the cell membranes. In this way, the contours of the cells including the cell membranes can be specified while the individual cells are kept independent. If the regions occupied by the individual cells in the specimen image are specified, a measurement (image cytometry) for a purpose is performed for each cell. By so doing, the quantitative information on the individual cells can be obtained.

As just described, in this embodiment, even if a multitude of cells are included in a specimen and are in contact with ouch other, quantitative information can be obtained on a cell-by-cell basis by individually discriminating the individual cells and performing necessary measurements. That is, a single-cell analysis is possible. Various combinations of the plurality of types of staining can be applied. Therefore, multiple immunostaining can be dealt with.

Note that the invention is not limited to the above embodiment and various changes other than the aforementioned ones can be made without departing from the gist of the invention. For example, although the region corresponding to the cell nucleus and the total region of the former region and the region corresponding to the cytoplasm are used as the "inner regions" of the invention in the above embodiment, there is no limitation to this. That is, the biological materials inward of the cell membrane can be stained or only the cell membrane is stained using at least one of membrane staining, nuclear staining and cytoplasmic staining, and the inner region can be extracted by detecting the biological materials from the specimen image.

Further, in the above embodiment, the learning model adopting deep learning as the machine learning algorithm is used for cell analysis. Learning is performed using pairs of the typical images and the ground truth images as the training data. However, the learning algorithm and the training data to be given to the learning algorithm are not limited to these. Various machine learning algorithms utilizable for the region division of images can be applied. Further, if biological materials serving as objects can be extracted by another imaging processing such as the threshold value processing or pattern matching, an extraction method not dependent on machine learning may be used in combination.

Further, in the above embodiment, alignment (registration) is performed among the plurality of specimen images. However, if such imaging is possible, in which position shifts among the respective specimen images can be ignored, registration can be omitted.

Further, in the above embodiment, the measurement (image cytometry) is performed for each cell after the cells in the specimen are individually discriminated. However, for example, one device can discriminate the individual cells by performing up to the extraction processing of the cell regions and output the discrimination result to outside, and the measurements can be performed by another device.

As the specific embodiment has been illustrated and described above, the specimen is a tissue section preferably having a thickness of less than 4 μm, more preferably having a thickness of 2 μm or less in the specimen analysis method according to this invention. In such a specimen, the erroneous recognition of individual cells due to the overlap of the cells in a thickness direction can be reduced.

Further, for example, if the plurality of types of staining includes the staining for selectively staining biological materials present only inward of cell membranes, inner regions can be extracted from a specimen image captured after such staining. Since the inner region extracted in this way corresponds to the biological materials present inward of the cell membrane in the cell, a probability that this extracted inner region is inside the cell can be said to be extremely high.

Further, for example, the region including the cell nucleus can be extracted as the inner region from the specimen image in which the cell nucleus is stained. The cell nucleus is a typical biological material present inward of the cell membrane. The cell nucleus is a relatively large structure in the cell and various methods for selectively staining cell nuclei have been established. Thus, the cell nuclei are suitable as biological materials indicating the presence of individual cells.

Further, for example, if the plurality of types of staining includes the staining for selectively staining cell membranes, an inner region may be extracted from a specimen image captured after such staining. Furthermore in this case, a region including a cell nucleus may be extracted as the inner region from a specimen image in which the cell membrane is stained and a specimen image in which the cell nucleus is stained. In the specimen image in which only the cell membrane is stained, a closed region surrounded by the stained cell membrane can be regarded as the inside of the cell. Thus, the inner region can be extracted using the specimen image in which the cell membrane is selectively stained. Particularly, by being used in combination with the specimen image in which the cell nucleus inside the cell is stained, the inner region of the cell can be more accurately extracted.

Further, for example, the image processing for expanding each point on the contour of the inner region toward the outside of the inner region can be performed until the expansion amount at each point reaches the specified value or the expanded contour contacts the other expanded inner region, and the total region of the inner region and the region expanded by this image processing can be set as the cell region. According to such a configuration, the cell region substantially coinciding with the region occupied by the actual cell can be specified by appropriately determining the specified value and expanding the extracted inner region to the region of the surrounding cell membrane.

Further, for example, the inner region can be extracted by inputting a specimen image to the learning model constructed by machine learning in advance and obtaining an output image. Cells in a specimen have large individual variations. Even in such a case, a learning model constructed by machine learning in advance using a multitude of case examples can be suitably utilized as a method for accurately extracting specific biological materials. Further, it is also possible to construct a highly versatile learning model applicable to various cells.

Further, for example, alignment may be performed utilizing positions corresponding to each other among a plurality of specimen images and inner regions may be extracted based on the plurality of aligned specimen images. In the case of repeatedly performing a staining operation and imaging, it is unavoidable that the position of the specimen is shifted every time the imaging is performed. To reduce a measurement error due to this position shift, it is effective to perform alignment based on a positional relationship of the positions corresponding to each other among the plurality of specimen images.

Further, for example, the specimen may be decolorized before the next staining is performed after the imaging. According to such a configuration, the influence of the previous staining result can be eliminated in the subsequent staining and imaging. Further, if the specimen not affected by the previous staining is individually imaged, a pseudo multiple immunostained image can be generated by synthesizing such specimen images.

This invention is useful for the analysis of a specimen including a multitude of cells and can be particularly suitably applied to an analysis process by an immunohistochemical method for a pathological specimen.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. A specimen analysis method, comprising:
obtaining a plurality of specimen images by successively applying a plurality of types of staining to a specimen to be evaluated and imaging the specimen after staining for at least two types of staining;
extracting an inner region being a closed region surrounded by a cell membrane and corresponding to inward of the cell membrane of a cell in the specimen by inputting at least one of the specimen images to a learning model constructed by machine learning in advance and obtaining an output image;
separating each extracted inner region as an individual cell included in the specimen from other inner region of other cells;
specifying a cell region corresponding to the individual cell by expanding the extracted inner region outwardly, and
performing image cytometry for the specified cell region based on the specimen images,
wherein the inner region is extracted based on the plurality of specimen images aligned with each other by executing alignment utilizing positions corresponding to each other among the plurality of specimen images,
wherein, for specifying the cell region:
an image processing which expands each point on a contour of the extracted inner region outwardly is performed until an expansion amount at the point reaches a predetermined specified value or a point on an expanded contour of the inner region contacts the other expanded inner region; and
a total region of the inner region and an expanded region by the image processing is specified as the cell region, and
wherein the inner region is extracted based on a combination of a plurality of the specimen images of different types of staining including a staining in which the cell membrane is selectively stained.

2. The specimen analysis method according to claim 1, wherein the specimen is a tissue section having a thickness of less than 4 μm.

3. The specimen analysis method according to claim 1, wherein the specimen is a tissue section having a thickness equal to or less than 2 μm.

4. The specimen analysis method according to claim 1, wherein
the inner region is extracted from a specimen image captured after a staining in which a biological material present only inside of the cell membrane is selectively stained out of the plurality of types of staining.

5. The specimen analysis method according to claim 1, wherein the specimen is decolorized before next staining after the imaging.

6. An image processing method using a plurality of specimen images obtained by successively applying a plurality of types of staining to a specimen to be evaluated and imaging the specimen after staining for at least two types of staining, the image processing method comprising:
extracting an inner region being a closed region surrounded by a cell membrane and corresponding to inward of the cell membrane of a cell in the specimen by inputting at least one of the specimen images to a learning model constructed by machine learning in advance and obtaining an output image;
separating each extracted inner region as an individual cell included in the specimen from other inner region of other cells;
specifying a cell region corresponding to the individual cell by expanding the extracted inner region outwardly, and
performing image cytometry for the specified cell region based on the specimen images,
wherein the inner region is extracted based on the plurality of specimen images aligned with each other by executing alignment utilizing positions corresponding to each other among the plurality of specimen images,
wherein for specifying the cell region:
an image processing which expands each point on a contour of the extracted inner region outwardly is performed until an expansion amount at the point reaches a predetermined specified value or a point on an expanded contour of the inner region contacts the other expanded inner region; and
a total region of the inner region and an expanded region by the image processing is specified as the cell region, and
wherein the inner region is extracted based on a combination of a plurality of the specimen images of different types of staining including a staining in which the cell membrane is selectively stained.

7. The specimen analysis method according to claim 1, wherein a closed region surrounded by the cell membrane and not including the cell membrane is extracted as the inner region.

8. The image processing method according to claim 6, wherein a closed region surrounded by the cell membrane and not including the cell membrane is extracted as the inner region.

* * * * *